(12) United States Patent
Hamouche

(10) Patent No.: US 11,684,403 B2
(45) Date of Patent: Jun. 27, 2023

(54) SYSTEM AND METHOD FOR INFLATING A CRYOABLATION BALLOON CATHETER

(71) Applicant: Boston Scientific Scimed Inc., Maple Grove, MN (US)

(72) Inventor: Chadi Hamouche, Quebec (CA)

(73) Assignee: Boston Scientific Scimed, Inc., Maple Grove, MN (US)

( * ) Notice: Subject to any disclaimer, the term of this patent is extended or adjusted under 35 U.S.C. 154(b) by 846 days.

(21) Appl. No.: 16/542,816

(22) Filed: Aug. 16, 2019

(65) Prior Publication Data

US 2020/0060746 A1    Feb. 27, 2020

Related U.S. Application Data

(60) Provisional application No. 62/720,565, filed on Aug. 21, 2018.

(51) Int. Cl.
*A61B 18/02* (2006.01)
*A61B 18/00* (2006.01)
*A61M 25/10* (2013.01)

(52) U.S. Cl.
CPC .... *A61B 18/02* (2013.01); *A61B 2018/00577* (2013.01); *A61B 2018/0212* (2013.01); *A61B 2018/0262* (2013.01); *A61M 25/10185* (2013.11); *A61M 2205/3344* (2013.01)

(58) Field of Classification Search
CPC .......... A61B 18/02; A61B 2018/00577; A61B 2018/0212; A61B 2018/0262; A61B 2018/0022; A61B 2018/00375; A61B 2090/064; A61M 25/10185; A61M 25/10181; A61M 2205/3344
See application file for complete search history.

(56) References Cited

U.S. PATENT DOCUMENTS 5,971,979 A * 10/1999 Joye ........................ A61B 18/02
128/898
2009/0299356 A1* 12/2009 Watson ............. A61M 25/1006
606/21

* cited by examiner

*Primary Examiner* — Khadijeh A Vahdat
(74) *Attorney, Agent, or Firm* — Nelson Mullins Riley & Scarborough LLP

(57) ABSTRACT

A system for inflating a cryogenic ablation catheter balloon, the system comprising a fluid source containing a fluid in a liquid state, a first supply line fluidly coupled to the fluid source and configured to be fluidly coupled to an internal space within the cryogenic ablation catheter balloon, the first supply line including an inline multi-stage pressure regulating system. The multi-stage pressure regulating system includes a first stage configured to cause the fluid to transition from the liquid state to a gas state, and a second stage downstream of the first stage configured to maintain the fluid downstream of the second stage at a pressure corresponding to an inflation pressure of cryogenic ablation catheter balloon.

9 Claims, 3 Drawing Sheets

SYSTEM AND METHOD FOR INFLATING A CRYOABLATION BALLOON CATHETER

CROSS REFERENCE TO RELATED APPLICATION

This application claims priority to Provisional Application No. 62/720,565, filed Aug. 21, 2018, which is herein incorporated by reference in its entirety.

TECHNICAL FIELD

The present invention relates to medical devices and methods for treating cardiac arrhythmias. More specifically, the invention relates to devices and methods for applying cryotherapy to cardiac tissues.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the user or operator) portion of the catheter, and often at the tip of the catheter.

Various forms of energy can be used to ablate diseased heart tissue. These can include radio frequency (RF), cryogenics, ultrasound and laser energy, to name a few. During a cryoablation procedure, with the aid of a guide wire, the distal tip of the catheter is positioned adjacent to targeted cardiac tissue, at which time energy is delivered to create tissue necrosis, rendering the ablated tissue incapable of conducting electrical signals.

Atrial fibrillation (AF) is a common arrhythmia treated using catheter ablation. One AF the treatment strategy involves isolating the pulmonary veins from the left atrial chamber. A particularly useful technique known as catheter balloon cryotherapy or cryoablation can be employed to treat AF. During balloon cryoablation procedures, a balloon on a balloon catheter is positioned within the ostium of the pulmonary vein to be treated, and inflated to intimately contact the surrounding tissue and occlude the pulmonary vein. Traditionally, the operator will inflate the balloon with no cooling fluid provided therein, and verify occlusion using methods such as injection contrast and fluoroscopy prior to delivering the ablative (i.e., cryogenic) energy.

There is a continuing need for improved systems and methods for controlling balloon inflation and cryo-therapy delivery for pulmonary vein isolation procedures.

SUMMARY

Example 1 is a system for inflating a cryogenic ablation catheter balloon, the system comprising a fluid source and a first supply line. The fluid source contains a fluid in a liquid state. The first supply line is fluidly coupled to the fluid source and is configured to be fluidly coupled to an internal space within the cryogenic ablation catheter balloon, and includes an inline multi-stage pressure regulating system. The multi-stage pressure regulating system includes a first stage configured to cause the fluid to transition from the liquid state to a gas state, and a second stage downstream of the first stage configured to maintain the fluid downstream of the second stage at a pressure corresponding to an inflation pressure of cryogenic ablation catheter balloon.

In Example 2, the system of Example 1, wherein the fluid source is maintained at a first pressure selected so as to maintain the fluid in the liquid state, and the first stage is configured to receive the fluid at substantially the first pressure and to discharge the fluid at a second pressure that is lower than the first pressure.

In Example 3, the system of Example 2, wherein the first pressure is at least 500 psig, and the second pressure is between about 30 psig and about 100 psig.

In Example 4, the system of either of Examples 2 or 3, wherein the second stage is configured to receive the fluid at the second pressure and discharge the fluid at the inflation pressure of the cryogenic ablation catheter balloon.

In Example 5, the system of any of Examples 1-4, wherein the inflation pressure is less than 30 psig.

In Example 6, the system of any of Example 1-5, wherein the first stage comprises a first pressure regulator and the second stage comprises a second pressure regulator.

In Example 7, the system of any of Examples 1-6, wherein the first stage comprises a first pressure sensor operatively coupled to a first proportional valve, and the second stage comprises a second pressure sensor operatively coupled to a second proportional valve.

In Example 8, the system of any of Examples 1-7, wherein the first supply line includes a first isolation valve positioned upstream or downstream of the multi-stage pressure regulating system.

In Example 9, the system of any of Examples 1-8, wherein the multi-stage pressure regulating system further comprises a third stage disposed downstream of the first stage and upstream of the second stage.

In Example 10, the system of any of Examples 1-9, wherein the first supply line is configured to be fluidly coupled to the internal space within the cryogenic ablation catheter balloon through a first port on the cryogenic ablation catheter.

In Example 11, the system of any of Examples 1-10, further comprising a second supply line fluidly coupled to the fluid source and configured to be fluidly coupled to the internal space within the cryogenic ablation catheter balloon.

In Example 12, the system of Example 11, wherein the second supply line is configured to be fluidly coupled to the internal space within the cryogenic ablation catheter balloon through a second port on the cryogenic ablation catheter.

Example 13 is a cryotherapy system comprising: the cryogenic ablation catheter balloon inflation system according to any of Examples 1-12, and a cryogenic ablation catheter comprising: a flexible shaft having a proximal end portion and a distal end portion; a handle assembly connected to the proximal end portion of the body; and an expandable balloon disposed about the distal end portion of the shaft and defining an internal space. The first and second supply lines of the cryogenic ablation catheter balloon inflation system are each configured to be in fluid communication with the internal space.

In Example 14, the cryotherapy system of Example 13, wherein the cryogenic ablation catheter further comprises first and second lumens within the shaft and in fluid communication with the internal space, and wherein the first supply line is configured to be in fluid communication with the first lumen, and the second supply line is configured to be in fluid communication with the second lumen.

In Example 15, the cryotherapy system of Example 14, wherein the first lumen is sized and configured to be operable as an exhaust lumen to enable evacuation of the fluid from the internal space.

Example 16 is a system for inflating a cryogenic ablation catheter balloon, the system comprising a fluid source containing a fluid in a liquid state, a first supply line fluidly coupled to the fluid source and configured to be fluidly coupled to a first port on the cryogenic ablation catheter, and an in-line, multi-stage pressure regulation system in the first supply line. The multi-stage pressure regulation system includes a first stage having a first inlet and a first outlet and configured to cause the fluid to transition from the liquid state at the first inlet to a gas state at the first outlet, and a second stage downstream of the first stage having a second inlet and a second outlet, the second stage configured to maintain the fluid downstream of the second stage in the gas state at a pressure corresponding to an inflation pressure of the cryogenic ablation catheter balloon.

In Example 17, the system of Example 16, wherein the fluid source is maintained at a first pressure selected so as to maintain the fluid in the liquid state, and the first stage is configured to receive the fluid at substantially the first pressure and to discharge the fluid at a second pressure that is lower than the first pressure, the second pressure selected so that the fluid transitions from the liquid state to the gas state across the first stage.

In Example 18, the system of Example 17, wherein the first pressure is at least 500 psig, and the second pressure is between about 30 psig and about 100 psig.

In Example 19, the system of Example 18, wherein the second stage is configured to receive the fluid at the second pressure and discharge the fluid at the inflation pressure of the cryogenic ablation catheter balloon.

In Example 20, the system of Example 19, wherein the inflation pressure is less than 30 psig.

In Example 21, the system of Example 20, wherein the first stage comprises a first pressure regulator and the second stage comprises a second pressure regulator.

In Example 22, the system of Example 21, wherein the first supply line includes a first isolation valve positioned upstream or downstream of the multi-stage pressure regulating system.

In Example 23 the system of Example 20, wherein the first stage comprises a first pressure sensor operatively coupled to a first proportional valve, and the second stage comprises a second pressure sensor operatively coupled to a second proportional valve.

In Example 24, the system of Example 16, wherein the multi-stage pressure regulating system further comprises a third stage disposed downstream of the first stage and upstream of the second stage.

In Example 25, the system of Example 16, further comprising a second supply line fluidly coupled to the fluid source and configured to be fluidly coupled to the internal space within the cryogenic ablation catheter balloon.

In Example 26, the system of Example 25, wherein the second supply line is configured to be fluidly coupled to the internal space within the cryogenic ablation catheter balloon through a second port on the cryogenic ablation catheter.

Example 27 is a cryotherapy system comprising a cryogenic ablation catheter and a cryogenic ablation catheter balloon inflation system. The cryogenic ablation catheter comprises a flexible shaft having a proximal end portion and a distal end portion, a handle assembly connected to the proximal end portion of the body, and an expandable balloon disposed about distal end portion of the shaft and defining an internal space. The cryogenic ablation catheter balloon inflation system comprises a fluid source containing a fluid in a liquid state, and a first supply line fluidly coupled to the fluid source and configured to be fluidly coupled to an internal space within the cryogenic ablation catheter balloon. The first supply line includes an inline multi-stage pressure regulating system, wherein the multi-stage pressure regulating system includes a first stage and a second stage. The first stage is configured to cause the fluid to transition from the liquid state to a gas state, and the second stage is downstream of the first stage and is configured to maintain the fluid downstream of the second stage at a pressure corresponding to an inflation pressure of cryogenic ablation catheter balloon.

In Example 28, the cryotherapy system of Example 27, wherein the cryogenic ablation catheter further comprises first and second lumens within the shaft and in fluid communication with the internal space, and wherein the first supply line is configured to be in fluid communication with the first lumen, and the second supply line is configured to be in fluid communication with the second lumen.

In Example 29, the cryotherapy system of Example 27, wherein the first lumen is sized and configured to be operable as an exhaust lumen to enable evacuation of the fluid In Example 30, the cryotherapy system of Example 29, wherein the first pressure is at least 500 psig, and the second pressure is between about 30 psig and about 100 psig.

In Example 31, the cryotherapy system of Example 30, wherein the second stage is configured to receive the fluid at the second pressure and discharge the fluid at the inflation pressure of the cryogenic ablation catheter balloon.

In Example 32, the cryotherapy system of Example 31, wherein the inflation pressure is less than 30 psig.

Example 33 is a method of inflating a cryogenic ablation catheter balloon, the method comprising directing a fluid from a fluid source at a first pressure and in a liquid state to an inlet of a multi-stage pressure regulating system fluidly coupled to an internal space defined by a cryogenic ablation catheter balloon, reducing a pressure of the fluid to a second pressure across a first stage of the multi-stage pressure regulating system, wherein the second pressure is selected such that the fluid transitions from the liquid state to a gas state at an outlet of the first stage, reducing the pressure of the fluid to an inflation pressure of the cryogenic ablation catheter balloon, and delivering the fluid to the internal space in a gas state.

In Example 34, the method of Example 33, wherein the first pressure is at least 500 psig, the second pressure is between about 30 psig and about 100 psig, and the inflation pressure is less than 30 psig.

In Example 35, the method of Example 33, wherein the first stage comprises a first pressure regulator and the second stage comprises a second pressure regulator.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
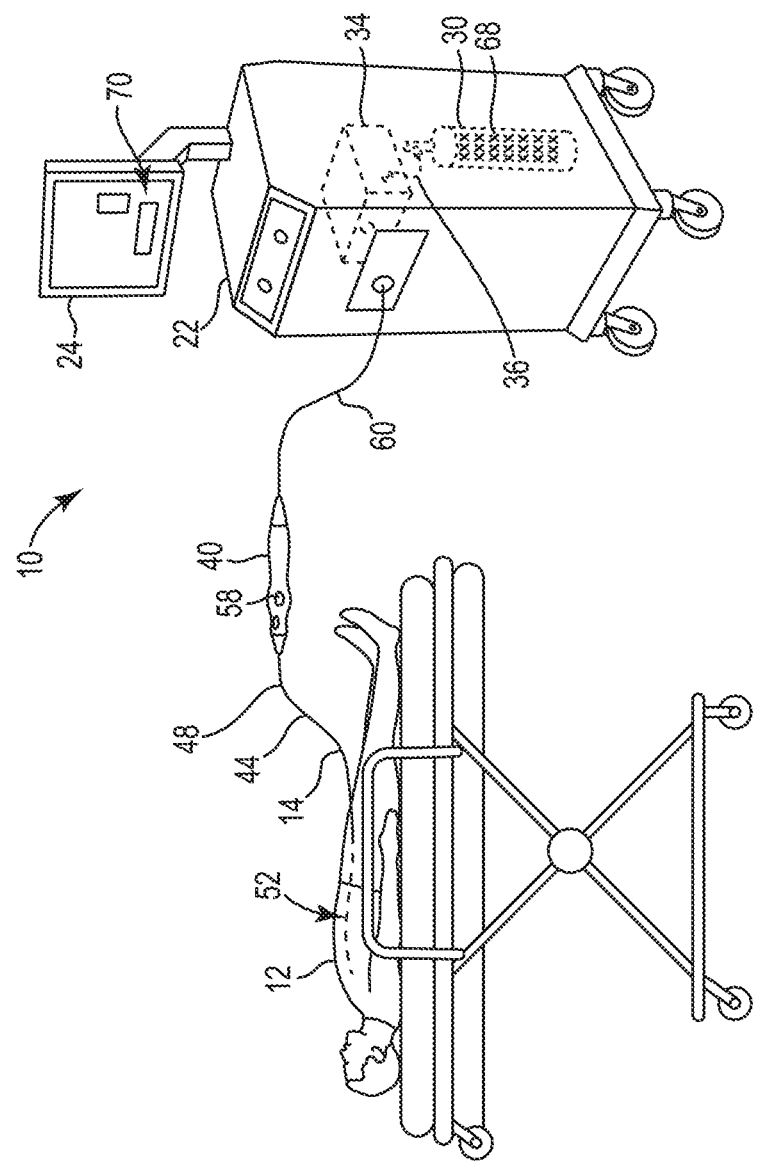
FIG. 1 is a simplified schematic side view illustration of a patient and one embodiment of a cryogenic balloon catheter system according to embodiments.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a simplified schematic side view illustration of an embodiment of a cryogenic balloon catheter system 10 for use with a patient 12, which can be a human being or an animal. Although the design of the cryogenic balloon catheter system 10 can be varied depending on the particular clinical needs of the patient 12, in the illustrated embodiment, the cryogenic balloon catheter system 10 can include one or more of a balloon catheter 14, a control console 22, a graphical display 24, and a fluid control system 28 (illustrated in phantom and disposed within the control console 22 in FIG. 1. In the illustrated embodiment, the fluid control system 28 includes a fluid source 30 and a fluid control arrangement 34. In the various embodiments, the fluid control system 28 can include various conduits, valves and instrumentation configured to supply and withdraw a fluid to the active elements on the balloon catheter 14 as will be described in greater detail elsewhere herein. In the illustrated embodiment, the fluid source 30 is operably connected to the fluid control arrangement 34 by a conduit 36 (which may be in the form of a hose or tubing) configured to transfer fluid contained within the fluid source 30 to components making up the fluid control arrangement 34.

As further shown, the balloon catheter 14 includes a handle assembly 40, and a shaft 44 having a proximal end portion 48 connected to the handle assembly 40, and a distal end portion 52, shown disposed within the patient 12 in FIG. 1. As will be appreciated, the handle assembly 40 can include various components, such as the control element 58 in FIG. 1, that the user can manipulate to operate the balloon catheter 14. Also, in the particular embodiment illustrated in FIG. 1, an umbilical 60 operatively connects the handle assembly 40 and the active components of the balloon catheter 14 to the control console 22.

In various embodiments, the system 10 may also include additional components or alternative approaches to operatively connect the balloon catheter 14 to the control console 22. That is, the particular means of operatively connecting these elements is not critical the present disclosure, and so any suitable means can be employed.

It is understood that although FIG. 1 illustrates the structures of the cryogenic balloon catheter system 10 in a particular position, sequence and/or order, these structures can be located in any suitably different position, sequence and/or order than that illustrated in FIG. 1. It is also understood that the cryogenic balloon catheter system 10 can include fewer or additional components than those specifically illustrated and described herein.

In various embodiments, the fluid control system 28 is configured to monitor and control various processes of the ablation procedures performed with the cryogenic balloon catheter system 10. More specifically, the fluid control system 28 can monitor and control release and/or retrieval of a cooling fluid 68, e.g., a cryogenic fluid (shown schematically contained within the fluid source 30 in FIG. 1), to the balloon catheter 14, e.g., via fluid injection and fluid exhaust lines (not shown, but which may be disposed within the umbilical 60. The fluid control system 28 can also control various structures that are responsible for maintaining and/or adjusting a flow rate and/or pressure of the cryogenic fluid 68 that is released to the balloon catheter 14 during the cryoablation procedure. In such embodiments, the cryogenic balloon catheter system 10 delivers ablative energy in the form of cryogenic fluid 68 to cardiac tissue of the patient 12 to create tissue necrosis, rendering the ablated tissue incapable of conducting electrical signals. Additionally, in various embodiments, the fluid control system 28 can control activation and/or deactivation of one or more other processes of the balloon catheter 14.

Further, or in the alternative, the fluid control system 28 can receive data and/or other information (hereinafter sometimes referred to as "sensor output") from various structures within the cryogenic balloon catheter system 10. In some embodiments, the fluid control system 28 can receive, monitor, assimilate and/or integrate the sensor output, and/or any other data or information received from any structure within the cryogenic balloon catheter system 10 in order to control the operation of the balloon catheter 14. As provided herein, in various embodiments, the fluid control system 28 can initiate and/or terminate the flow of cryogenic fluid 68 to the balloon catheter 14 based on the sensor output.

As shown in FIG. 1, in certain embodiments, the fluid control system 28 can be positioned substantially within the control console 22. Alternatively, at least a portion of the fluid control system 28 can be positioned in one or more other locations within the cryogenic balloon catheter system 10, e.g., within the handle assembly 40.

The fluid source 16 contains the cryogenic fluid 68, which is delivered to and from the balloon catheter 14 with or without input from the fluid control system 28 during a cryoablation procedure. Once the ablation procedure has initiated, the cryogenic fluid 68 can be delivered and the resulting gas, after a phase change, can be retrieved from the balloon catheter 14, and can either be vented or otherwise discarded as exhaust. Additionally, the type of cryogenic fluid 68 that is used during the cryoablation procedure can vary. In one non-exclusive embodiment, the cryogenic fluid 68 can include liquid nitrous oxide. However, any other suitable cryogenic fluid 68 can be used. For example, in one non-exclusive alternative embodiment, the cryogenic fluid 68 can include liquid nitrogen.

The design of the balloon catheter 14 can be varied to suit the specific design requirements of the cryogenic balloon catheter system 10. As shown, the balloon catheter 14 is inserted into the body of the patient 12 during the cryoablation procedure. The handle assembly 40 can be handled and used by the operator to operate, position and control the balloon catheter 14. The design and specific features of the handle assembly 40 can vary to suit the design requirements of the cryogenic balloon catheter system 10. In the embodiment illustrated in FIG. 1, the handle assembly 40 is separate from, but in electrical and/or fluid communication with the fluid control system 28, the fluid source 16, and the graphical display 24. In some embodiments, the handle assembly 40 can integrate and/or include at least a portion of the fluid control system 28 within an interior of the handle assembly 40. It is understood that the handle assembly 40 can include fewer or additional components than those specifically illustrated and described herein. Additionally, in certain embodiments, the handle assembly 40 can include circuitry (not shown in FIG. 1) that can include at least a portion of the fluid control system 28. Alternatively, the circuitry can transmit electrical signals such as the sensor output, or otherwise provide data to the fluid control system 28 as described herein. In one embodiment, the circuitry can include a printed circuit board having one or more integrated circuits, or any other suitable circuitry.

Still further, in certain embodiments, the handle assembly 40 can be used by the operator to initiate and/or terminate the cryoablation process, e.g., to start the flow of the cryogenic fluid 68 to the balloon catheter 14 in order to ablate certain targeted heart tissue of the patient 12.

In the embodiment illustrated in FIG. 1, the control console 22 includes at least a portion of the fluid control system 28, the fluid source 16, and the graphical display 24. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the graphical display 24.

During cryoablation procedures, the balloon catheter 14 and the control console 22 must be mechanically connected to allow the flow of cryogenic fluid 68 from the control console 22 to the balloon catheter 14 and back to the control console 22. Generally, during the application of ablative energy, the cryogenic fluid 68 flows in a liquid phase to the balloon catheter 14. The cryogenic fluid 68 then undergoes a phase change and returns to the control console 22 as exhaust in a gaseous phase.

In various embodiments, the graphical display 24 is electrically connected to the fluid control system 28. Additionally, the graphical display 24 provides the operator of the cryogenic balloon catheter system 10 with information that can be used before, during and after the cryoablation procedure. For example, the graphical display 24 can provide the operator with information based on the sensor output, and any other relevant information that can be used before, during and after the cryoablation procedure. The specifics of the graphical display 24 can vary depending upon the design requirements of the cryogenic balloon catheter system 10, or the specific needs, specifications and/or desires of the operator.

In one embodiment, the graphical display 24 can provide static visual data and/or information to the operator via various frames or other representations (depicted as element 70 in FIG. 1). In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

Figure 2:
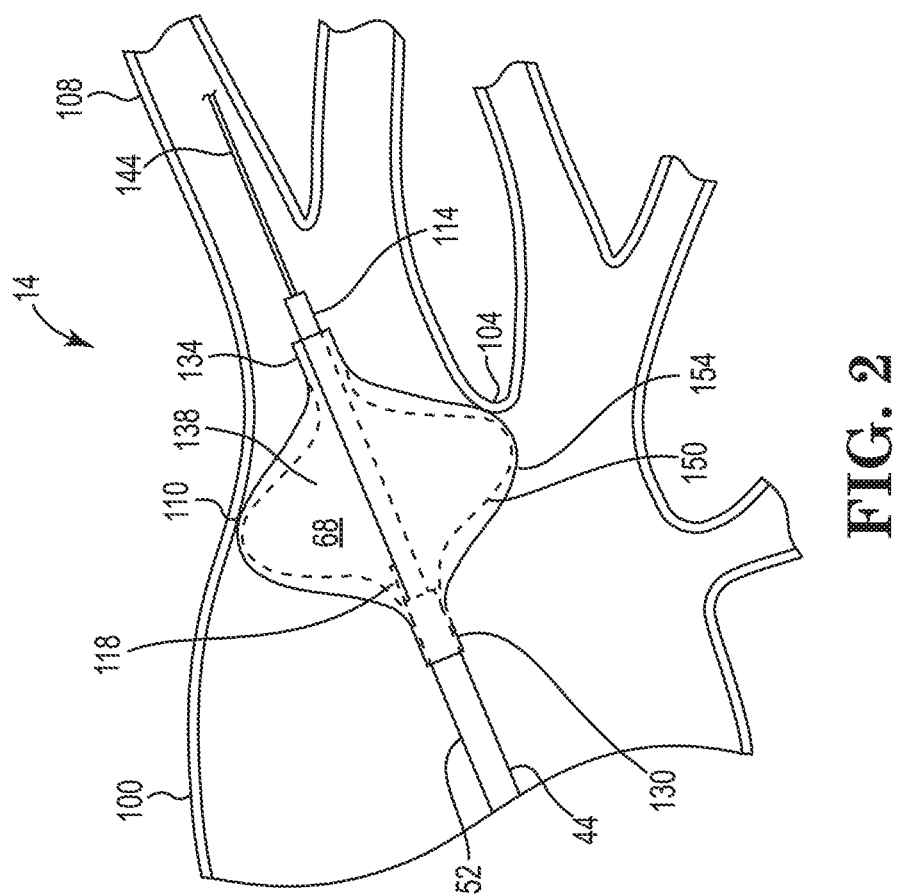
FIG. 2 is a simplified schematic view illustration of a portion of the patient and a portion of an embodiment of the cryogenic balloon catheter system.

FIG. 2 is a schematic illustration of the distal end portion 52 of the balloon catheter 14 positioned within a selected anatomical region of the patient 12, in this case, a left atrium 100 adjacent to an ostium 104 of a pulmonary vein 108, such as when the system 10 is used in a pulmonary vein isolation (PVI) procedure to terminate an atrial fibrillation. In the illustrated embodiment, the balloon catheter 14 includes an expandable balloon 110, a guidewire lumen 114 and an injection tube 118. As shown, the balloon 110 has a proximal end 130 and an opposite distal end 134, and defines an internal space 138 that creates a cryo-chamber during a cryoablation procedure. In the illustrated embodiment, the proximal end 130 of the balloon 110 is attached to the distal end portion 52 of the shaft 44, and the distal end 134 of the balloon 110 is attached to the guidewire lumen 114 near the distal end thereof. In the illustrated embodiment, the injection tube 118 is disposed within and extends from the shaft 44, and terminates within and is open to the internal space 138. The injection tube 118 is operable to deliver the cryogenic fluid 68 to the internal space 138.

Although not shown in FIG. 2, the balloon catheter 14 also includes an exhaust lumen within the shaft 44 and open to the internal space 138. The exhaust lumen is operable to facilitate evacuation of the cryogenic fluid 68 from the internal space 138, and also to facilitate inflation of the balloon 110 as will be explained in further detail herein.

In various embodiments, the guidewire lumen may be slidable relative to the shaft 44 to facilitate expansion and subsequent collapse of the balloon 110 in use. However, the particular construction of the balloon 110 and guidewire lumen 114 is not critical to the present disclosure, and so other configurations may be used within the scope of the various embodiments.

For illustration purposes, an instrument 144 is shown extending through and beyond the guidewire lumen and into the pulmonary vein 108. As the skilled artisan will appreciate, the instrument 144 may be a guidewire, mapping wire or catheter, anchoring wire, or other medical device useful to facilitate the particular cryo-therapy procedure. However, the use of the instrument 144 is optional and is not critical to the embodiments disclosed herein.

In the embodiment of FIG. 2, the balloon 110 is a dual-balloon construction including an inner balloon 150 and an outer balloon 154. The balloons 150, 154 are configured such that the inner balloon 150 receives the cryogenic fluid 68 (illustrated in FIG. 1), and the outer balloon 154 surrounds the inner balloon 150. The outer balloon 154 acts as part of a safety system to capture the cryogenic fluid 68 in the event of a leak from the inner balloon 150. It is understood that the balloon catheter 14 can include other structures as well. However, for the sake of clarity, these other structures have been omitted from the figures. Additionally, it is further appreciated that in some alternative embodiments, the balloon catheter 14 includes only a single balloon.

In the embodiment illustrated in FIG. 2, the balloon catheter 14 is positioned within the left atrium 100 of the patient 12. The guidewire 144 and guidewire lumen 114 are inserted into a pulmonary vein 108 of the patient 12, and the catheter shaft 44 and the balloons 150, 154 are moved along the guidewire 144 and/or the guidewire lumen 114 to be positioned near an ostium 104 of the pulmonary vein 108.

During use, the inner balloon 150 can be partially or fully inflated so that at least a portion of the inner balloon 150 expands against at least a portion of the outer balloon 154. Once the inner balloon 150 is sufficiently inflated, an outer surface of the outer balloon 154 can then be positioned to abut and/or substantially form a seal with the ostium 104 of the pulmonary vein 108 to be treated.

The inner balloon 150 and the outer balloon 154 can be formed from any suitable materials. For example, in some embodiments, the inner balloon 150 can be formed from a sturdy material to better inhibit leaks of the cryogenic fluid 68 that is received therein, and the outer balloon 154 can be made from a relatively compliant material to ensure better contact and positioning between the outer balloon 154 and the pulmonary vein 108.

During balloon cryoablation procedures, prior to delivering the cryoablative energy, the operator can inflate the balloon using the cryogenic fluid 68 at a relatively high temperature (i.e., well above the temperature sufficient to ablate the target tissue). In this way, the operator can ensure sufficient balloon-tissue contact and vein occlusion before starting an ablation to increase probability of vein isolation. In addition, to minimize procedure time, it can be desirable to utilize the exhaust lumen of the balloon catheter 14 as a conduit for delivering the cryogenic fluid 68 to the internal space 138 during the inflation phase, i.e., due to its relatively large size compared to the injection tube 118. It is also desirable to maintain relatively close control over the inflation pressure during the cryoablation procedure. For example, a drop in the inflation pressure can result in partial deflation of the balloon 110 and consequent or diminishment of balloon tissue contact and vessel occlusion.

Figure 3:
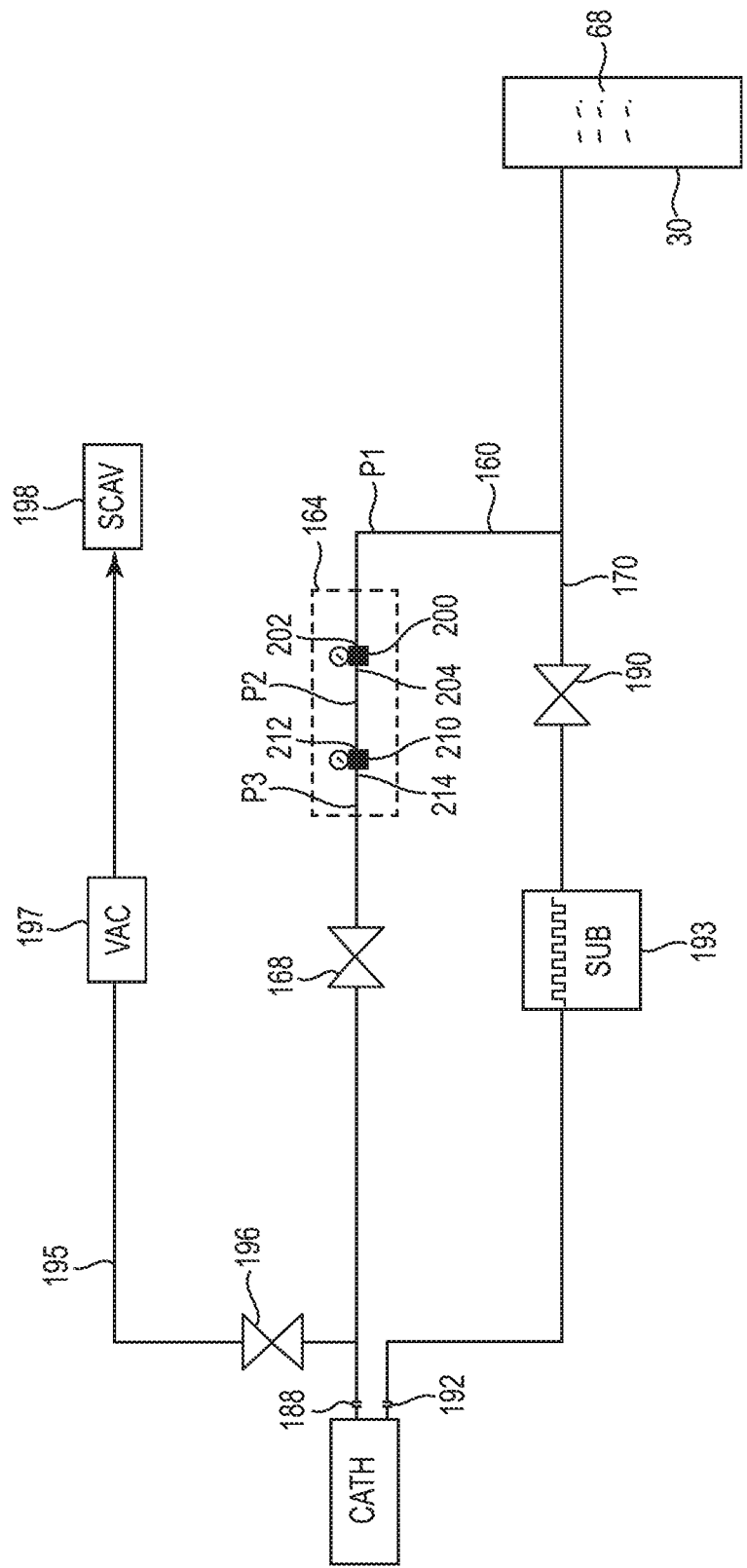
FIG. 3 is a schematic diagram of a cryogenic balloon catheter inflation system according to an embodiment.

FIG. 3 is a schematic diagram of the fluid control system 28 according to an embodiment of the present disclosure. In the illustrated embodiment, the fluid control system 28 includes the fluid source 30 and the fluid control arrangement 34, which are operatively and fluidly coupled together via the conduit 36. As further shown, the fluid control arrangement 34 includes an inflation line 160 and an injection line 170. As shown, the inflation line 160 includes an inline pressure regulating system 180 and an inflation line valve 168, and is operatively coupled to a return port 188 on the balloon catheter 14. Additionally, the injection line 170 includes an injection line valve 190 and is operatively coupled to an injection port 192 on the balloon catheter 14.

In embodiments, the return port 188 and the injection port 190 of the balloon catheter 14 are in fluid communication, respectively, with the exhaust lumen and the injection tube 118 of the balloon catheter 14 described above. As such, the operative connection of the inflation line 160 to the return port 188 fluidly couples the inflation line 160 to the exhaust lumen and the internal space 138 of the balloon catheter 14. Similarly, the operative connection of the injection line 170 to the injection port 190 fluidly couples the injection 170 to the injection tube 118 and also the internal space 138 of the ablation catheter 14. The illustrated configuration thus allows both of the inflation and injection lines 160, 170 to be used to deliver the cryogenic fluid 68 to the internal space 138 to rapidly inflate the balloon 110 while providing for precise control over the inflation pressure, as will be described in greater detail below.

As further shown in FIG. 3, a subcooler 193 is also associated with the injection line 170, so that the injection line 190 can also operate for delivery of the cryogenic fluid 68 at cryogenic temperatures during the treatment phase of the cryoablation procedure. Generally speaking, the subcooler 193 is not operational during the process of inflating the balloon 110, and is thus need not be discussed further herein.

Additionally, FIG. 3 illustrates an exhaust line 195 fluidly coupled to the return port 188 of the ablation catheter 14. As shown, the exhaust line 195 includes an exhaust line valve 196 and a vacuum pump 197, and is operatively connected to a scavenging system 198 (e.g., via a wall-mounted port in the electrophysiology lab). The exhaust line 195 is operable to evacuate the cryogenic fluid 68 from the ablation catheter 14 and thereby effect deflation of the balloon 110 as per the needs of the operator, as is well known in the art. The exhaust line 195 is shown for illustration purposes only and is not used during the inflation process, and thus also need not be further discussed herein.

For various reasons that will be understood by those skilled in the art, the fluid source 30 operates at an internal pressure sufficient to maintain the cryogenic fluid 68 in a liquid state. However, the inflation pressure of the balloon 110 is, in the various embodiments, significantly lower than the fluid source 30 pressure, i.e., the cryogenic fluid 68 is gaseous at the balloon inflation pressure and non-cryogenic temperatures.

In the various embodiments, the multi-stage pressure regulating system 164 operates to reduce the working pressure of the cryogenic fluid 68 from the relatively high pressure at the fluid source 30 (at which the cryogenic fluid is in the liquid state) to the lower inflation pressure of the balloon 110. As such, the temperature of the cryogenic fluid 68 undergoes a substantial temperature drop across the multi-stage pressure regulating system 164 as a result of the well-known Joule-Thomson effect.

To counteract potentially undesired effects of the aforementioned Joule-Thomson cooling of the cryogenic fluid 68 in the inflation line 160, the multi-stage pressure regulating system 164 includes a first stage 200 having a first stage inlet 202 and a first stage outlet 204, and a second stage 210 having a second stage inlet 212 and a second stage outlet 214. In embodiments, the cryogenic fluid pressure P1 at the first stage inlet 202 is substantially equivalent to the operating pressure of the fluid source 30, and thus the first stage 200 receives the cryogenic fluid 68 in a liquid state. The first stage 200 is configured to reduce the operating pressure of the cryogenic fluid 68 to an intermediate pressure P2 at the first stage outlet 204 that is selected such that the cryogenic fluid 68 transitions from the liquid state to a gaseous state.

In embodiments, the second stage 210 is configured to reduce the operating pressure of the cryogenic fluid 68 (which is in a gas state at the second stage inlet 212) to a pressure P3 at the second stage outlet 214 corresponding to the inflation pressure of the balloon 110.

In embodiments, the cryogenic fluid 68 will undergo significant Joule-Thomson cooling across the first stage 200. And while some degree of Joule-Thomson cooling will also occur across the second stage 210 as a result of the expansion of the gaseous cryogenic fluid 68 from the second stage inlet 212 to the second stage outlet 214, this temperature change is well within the operational range of the second stage 210. At the same time, because the precise inflation pressure control is performed by the second stage 210, any potentially adverse effects (e.g., drift) resulting from the more substantial temperature drop occurring across the first stage 200 will only affect the first stage 200 and will have a minimal effect on the overall performance of the fluid control system 28 (if any effect at all).

Without in any way limiting the scope of the present disclosure, in embodiments, exemplary values for the pressure P1 may be 500 psig or greater. In embodiments, the pressure P2 may be between about 30 psig and 100 psig. In embodiments, the inflation pressure P3 may be less than about 30 psig. It is important to note, however, that the specific values selected for P1, P2 and P3 are not critical, and may vary depending on the particular system and other factors such as the type of cryogenic fluid 68 being used. That is, the actual pressure settings utilized may deviate from the examples above, so long as the cryogenic fluid 68 is in a gas state at the second stage inlet 212.

In the illustrated embodiment, the first and second stages 200, 210 each are shown comprising respective pressure regulators such as are well known in the art. In other embodiments, one or both of the first and second stages 200, 210 may include other means for pressure reduction and/or control, e.g., a proportional pressure control valve and pressure sensor operatively connected to a pressure controller.

Although FIG. 3 depicts the multi-stage pressure regulating system 164 having two stages, in alternative embodiments more than two stages can be employed. For example, in an embodiment, an intermediate stage can be disposed between the first and second stages 200, 210 illustrated in FIG. 3. In short, the particular number of pressure reduction stages utilized is not critical, so long as the multi-stage pressure regulating system 164 is configured so that the cryogenic fluid 68 enters the second stage inlet 212 (i.e., the inlet to the downstream-most stage) in the gas state to minimize the degree of Joule-Thomson cooling that will occur across that stage.

It is understood that although a number of different embodiments of the cryogenic balloon catheter system 10 have been illustrated and described herein, one or more features of any one embodiment can be combined with one or more features of one or more of the other embodiments, provided that such combination satisfies the intent of the present invention.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

I claim:

1. A system for inflating a cryogenic ablation catheter balloon, the system comprising:
    a fluid source containing a fluid, wherein the fluid source is configured to be maintained at a first pressure selected so as to maintain the fluid in a liquid state within the fluid source, and wherein the first pressure is at least 500 psig;
    a first supply line fluidly coupled to the fluid source and configured to be fluidly coupled to a first port on the cryogenic ablation catheter,
    an in-line, multi-stage pressure regulation system in the first supply line, the multi-stage pressure regulation system including:
        a first stage having a first inlet and a first outlet and configured to cause the fluid to transition from the liquid state at the first inlet to a gas state at the first outlet, wherein the first stage is configured to receive the fluid at substantially the first pressure and to discharge the fluid at a second pressure that is lower than the first pressure, wherein the second pressure is between 30 psig and 100 psig and is selected so that the fluid transitions from the liquid state to the gas state across the first stage, and wherein the first stage comprises a first pressure regulator;
        a second stage downstream of the first stage having a second inlet and a second outlet, the second stage configured to receive the fluid at the second pressure and discharge the fluid at an inflation pressure of the cryogenic ablation catheter balloon, wherein the inflation pressure is less than 30 psig, wherein the second stage comprises a second pressure regulator.

2. The system of claim 1, wherein the first supply line includes a first isolation valve positioned upstream or downstream of the multi-stage pressure regulating system.

3. The system of claim 1, further comprising a second supply line fluidly coupled to the fluid source and configured to be fluidly coupled to the internal space within the cryogenic ablation catheter balloon.

4. The system of claim 3, wherein the second supply line is configured to be fluidly coupled to the internal space within the cryogenic ablation catheter balloon through a second port on the cryogenic ablation catheter.

5. A cryotherapy system comprising:
    a cryogenic ablation catheter comprising:
        a flexible shaft having a proximal end portion and a distal end portion;
        a handle assembly connected to the proximal end portion of the flexible shaft; and
        an expandable balloon disposed about distal end portion of the flexible shaft and defining an internal space of the expandable balloon; and
    a cryogenic ablation catheter balloon inflation system comprising:
        a fluid source containing a fluid, wherein the fluid source is configured to be maintained at a first pressure selected so as to maintain the fluid in a liquid state within the fluid source;
        a first supply line fluidly coupled to the fluid source and configured to be fluidly coupled to the internal space of the cryogenic ablation catheter balloon, the first supply line including an inline multi-stage pressure regulating system, wherein the multistage pressure regulating system includes:
            a first stage configured to receive the fluid in the liquid state at substantially the first pressure and to discharge the fluid at a second pressure that is lower than the first pressure, the second pressure selected to cause the fluid to transition from the liquid state to a gas state across the first stage, wherein the first stage comprises a first pressure regulator, and
            a second stage downstream of the first stage configured to receive the fluid in the gas state at the second pressure and discharge the fluid at an inflation pressure of the cryogenic ablation catheter balloon that is lower than the second pressure, wherein the second stage comprises a second pressure regulator; and
        a second supply line fluidly coupled to the fluid source, wherein the first supply line and the second supply line of the cryogenic ablation catheter balloon inflation system are each configured to be in fluid communication with the internal space.

6. The cryotherapy system of claim 5, wherein the cryogenic ablation catheter further comprises a first lumen within the flexible shaft in fluid communication with the internal space, and a second lumen within the flexible shaft and in fluid communication with the internal space, and wherein the first supply line is configured to be in fluid communication with the first lumen, and the second supply line is configured to be in fluid communication with the second lumen.

7. The cryotherapy system of claim 6, wherein the first lumen is sized and configured to be operable as an exhaust lumen to enable evacuation of the fluid from the internal space.

8. The cryotherapy system of claim 7, wherein the first pressure is at least 500 psig, and the second pressure is between 30 psig and 100 psig.

9. The cryotherapy system of claim 8, wherein the inflation pressure is less than 30 psig.

* * * * *